United States Patent [19]
Grandfils et al.

[11] Patent Number: 5,962,566
[45] Date of Patent: Oct. 5, 1999

[54] BIOCOMPATIBLE AND BIODEGRADABLE NANOPARTICLES DESIGNED FOR PROTEINACEOUS DRUGS ABSORPTION AND DELIVERY

[75] Inventors: Christian Grandfils, Beerse; Robert Jerome, Sart-Jalhay; Nicole Nihant, Battice; Philippe Teyssie, Neuville en Condroz, all of Belgium

[73] Assignee: European Community, Luxembourg, Luxembourg

[21] Appl. No.: 08/973,863

[22] PCT Filed: Jul. 2, 1996

[86] PCT No.: PCT/EP96/02878

§ 371 Date: May 7, 1998

§ 102(e) Date: May 7, 1998

[87] PCT Pub. No.: WO97/02022

PCT Pub. Date: Jan. 23, 1997

[30] Foreign Application Priority Data

Jul. 5, 1995 [EP] European Pat. Off. .............. 95110445

[51] Int. Cl.⁶ ..................................................... A61K 9/51
[52] U.S. Cl. ......................... 524/378; 524/539; 424/499; 424/501; 424/78.38; 514/2; 514/171; 525/415; 525/450
[58] Field of Search ..................................... 424/499, 501, 424/78.38; 514/2, 171; 525/415, 450; 524/378, 539

[56] References Cited

U.S. PATENT DOCUMENTS 4,548,922 10/1985 Carey et al. ............................ 514/171
5,145,684 9/1992 Liversidge et al. ..................... 424/499

FOREIGN PATENT DOCUMENTS 0275796 7/1988 European Pat. Off. .
0520888 12/1992 European Pat. Off. .
0529711 3/1993 European Pat. Off. .
88/08011 10/1988 WIPO .
91/15193 10/1991 WIPO .

*Primary Examiner*—Andrew E. C. Merriam
*Attorney, Agent, or Firm*—Oblon, Spivak, McClelland, Maier & Neustadt, P.C.

[57] ABSTRACT

The presently claimed invention comprises a biopolymer nanoparticle for drug delivery wherein the nanoparticle comprises a homogeneous blend of an aliphatic polyester polymer blended with a polyether, a lipophilic or polypeptide drug and a biocompatible cholesterol interacting agent for preserving the activity of the drug administered to the patient while at the same time controlling the release of the drug. Methods for making the homogeneous drug delivery nanoparticles are also disclosed.

11 Claims, 5 Drawing Sheets

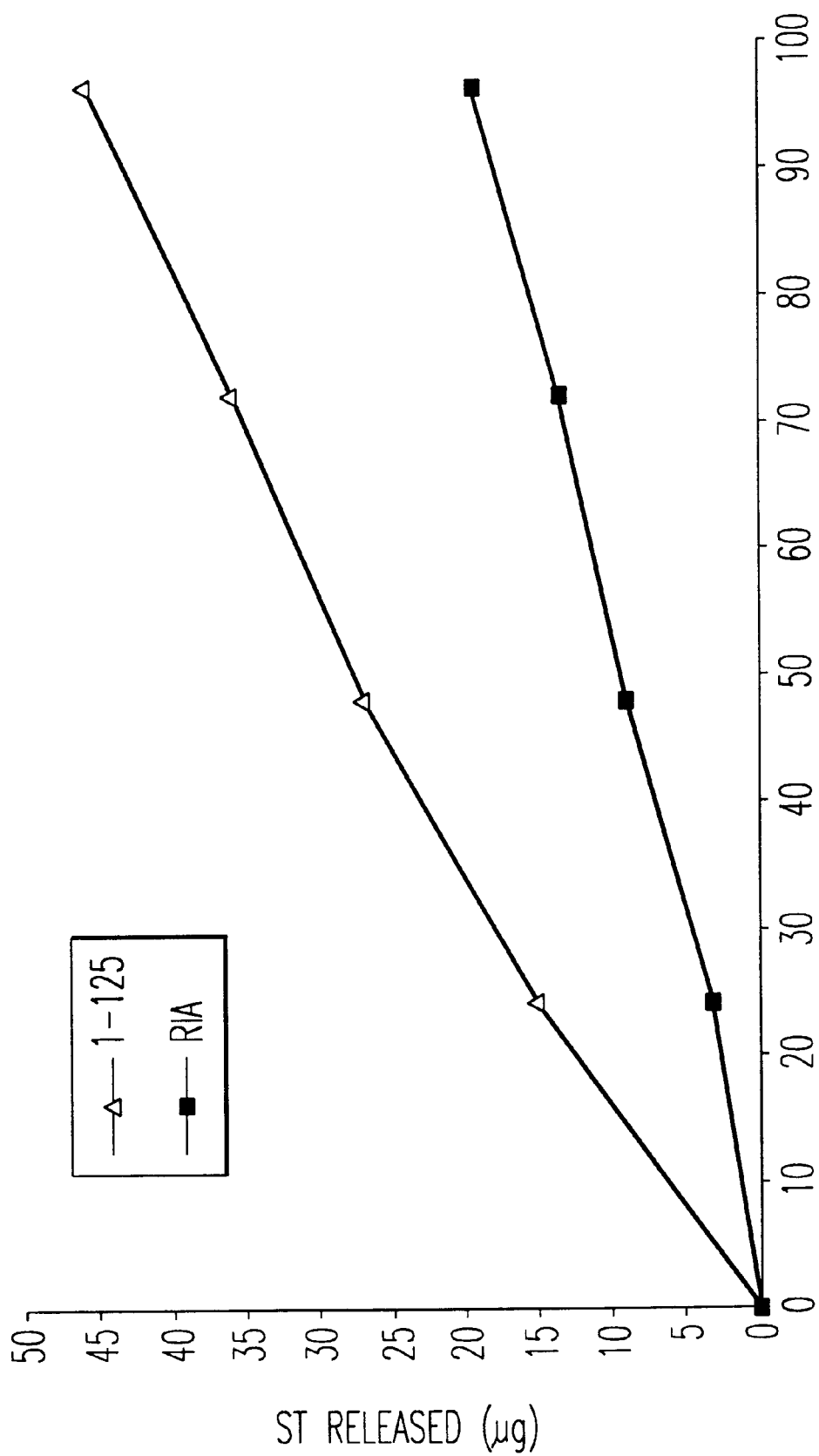

BIOCOMPATIBLE AND BIODEGRADABLE NANOPARTICLES DESIGNED FOR PROTEINACEOUS DRUGS ABSORPTION AND DELIVERY

BACKGROUND OF THE INVENTION

1. Field of the Invention

The invention is related with a polymer blend as an intermediate product for preparing nanoparticles, a process for preparing the polymer blend, a process for preparing nanoparticles and the nanoparticles obtainable by this process as well as method of treating patients with drugs or drug combinations adhered on or incorporated in nanoparticles.

2. Description of the Background

Nanoparticles in form of pseudolatex are derived from an oil-in-water submicron emulsion that is converted to colloidal polymer dispersion after removal of the organic solvent, used to dissolve the preformed polymer. Thus, they differ from most common latex prepared from water insoluble monomers by emulsion or dispersion polymerization. The major advantage of pseudolatexes relies upon the feasibility to convert most polymers into an organic colloidal dispersion allowing direct incorporation of plasticizers. Pseudolatexes of ethylcellulose in celluloseacetatephtalat have been used for pharmaceutical coating applications (Banker et al., Pharmaceutical Technology 1981, pp 55–61).

Nanocapsules of polylactide of size centered around 220 nm were reported Amnoury in J. Pharm. Sci., 1990, pp 763–767. The nanocapsules were prepared by an interfacial deposition technique. This method was applied for encapsulation of indomethacin.

Nanoencapsulation of low molecular weight antibiotic in polylactide-glycolide material was reported by Julienne et al., Proceed. Intern. Symp. Control. Rel. Bioact. Mater., 1989, pp 77–78.

Bazile et al. reported in Biomaterials 1992, pp 1093–1102 about the preparation of nanoparticles of polylactide (90 to 250 nm) coated with albumin. The protein was used as stabilizer of the oil-in-water emulsion without mentioning any encapsulation of an active drug and its sustained release.

Gref et al. in Science 1994, 263, pp 1600–1603 have described the formulation of polylactide (or polycaprolactone)-polyethyleneglycol block copolymer in 140 nm pseudolatexes. The amphiphilic copolymers has been used to encapsulate low molecular weight compounds that are released in some hours in vivo.

Nanoparticles are used as drug delivery systems. In colloidal drug delivery systems, edited by Jorg Kreuter, Marcel Dekker, Inc., New York, Basel, Hong Kong, pp 219–341, the significance of nanoparticles is described as well as conventional methods for producing such nanoparticles. Biodegradable pseudo-latex particles (nanoparticles) have been prepared from biocompatible polyesters by conventional emulsification/solvent diffusion methods. The coating polymer is initially dissolved in a water immiscible chlorinated organic solvent (or in mixtures of chlorinated and more polar solvents). Size of the particles usually exceeds 100 nm and no information is available about the effective encapsulation of especially protein drugs. Although, nanoparticles have been proven to be useful tools for drug delivery systems. Some problems relating to the control of particle size as well as particle loading with protein drugs are not solved. Also a high loading, a safeguarding drug activity and allowing for controlled drug release is a feature which is hard to match.

SUMMARY OF THE INVENTION

Subject of the present invention is to improve nanoparticles for the purpose of serving as drug delivery systems in particular for proteins or polypeptides. The nanoparticles of the invention which are obtainable by a process of the invention using a polymer blend of the invention solve the problems addressed above. The polymer blend of the invention which is an intermediate product for the preparation of the nanoparticles of the invention and can be prepared according to a process of the invention.

DETAILED DESCRIPTION OF THE INVENTION

The polymer blend according to claim 1 is obtainable by a process comprising the steps of intimate mixing a biocompatible polymer able to form nanoparticles and a biocompatible interacting agents for making the polymeric blend acceptable for a drug to be administered which interacting agent is able to preserve the activity of the drug to be administered and which interacting agent is able to control the release of the drug to be administered.

Preferably, the biocompatible polymer is a polymer which can be readily melted or used in a solvent deposition process for preparing nanoparticles. If the polymer can be readily melted this is quite convenient since it must not be dissolved and can be directly mixed intimately with the biocompatible interacting agent. During the melting process the polymer should not be decomposed or start to decompose.

When the biocompatible polymer is to be dissolved, preferably organic solvents are used. In particular, the biocompatible polymer is an aliphatic polyester such as poly-ε-caprolactone, polylactide or polyglycolide, or a copolymer thereof. Preferably, poly(D,L)lactide or poly(D,L)lactide-co-glycolide are used in particular in a 50% : 50% molar ratio. The polymer molecular weight is preferably in the range from 10.000 to several hundreds of thousand in particular from 20.000 to 50.000.

The biocompatible interacting agent is a polymer containing alcohol, ether and/or ester constitutive units. Preferably, the biocompatible interacting agent is either a polyether or polyvinyl alcohol. The preferred polyether is a polyethylene glycol or a plyoxyethylene-polyoxypropylene-polyoxyethylene triblock copolymer having in particular the general formula:

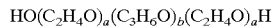

$$HO(C_2H_4O)_a(C_3H_6O)_b(C_2H_4O)_aH$$

wherein the lit a and b are selected to give molecular weight of the polyesters in the range of some hundreds to 20.000, preferably about 8.500, preferably lit a=75 and b=30. Such compounds are named poloxamers. Typically, the biocompatible interacting agent is present in the polymer blend composition between 10 and 60% by weight, preferably about 50% by weight.

The biocompatible interacting agent can be also an amphilic graft copolymer containing an hydrophilic backbone grafted with hydrophobic aliphatic polyester subchains. The synthesis of these copolymers has been previously described by Barakat et al. (J. Polym. Sci. A. Polym. Chem. 1994, 32, 2099–2110). The hydrophilic/lipophilic balance of the copolymer can be controlled by the comonomer molar ratio, the molecular weight of polylactide chains and the nature of the hydrophilic comonomer, e.g. polyhydroxyethylmethacrylate (HEMA), acrylamide, and N-vinylpyrrolidone. These copolymners can be directly dissolved together with the biocompatible polymer so that the preliminary step of blending may be avoided.

The polymeric blend of the invention is used to prepare the nanoparticles of the present invention. The polymer blend is an intermediate product which is manufactured according to the following process. The biocompatible polymer is for example melted together or prior to the addition of the interacting agent. The two components are thoroughly mixed and the mixture is then ready to be used for preparing the nanoparticles of the invention.

Alternatively, the components are dissolved in an organic solvent and poured together under mixing. After combining the solution the solvent is evaporated. For example, the polymers are simultaneously dissolved in an organic solvent preferably acetone or a chlorinated solvent at room temperature. The concentration of each polymer is in the range of 1 to 10% by weight, preferably about 3 to 5% by weight. The solvent can be evaporated under a nitrogen flux at ambient temperature and subsequently at 40° C. until dryness.

The nanoparticles of the invention can be prepared by the process of the invention comprising the steps of:

dissolving the polymer blend as described above in an organic solvent, adding a biocompatible surfactant and a drug or drug combination, in such a manner that the mixture of polymer blend, surfactant and drug or drug combination forms an essentially homogenous mixture and contacting the mixture with an aqueous phase to form a dispersion and separate the formed nanoparticles from the liquid phase.

The dissolution of the polymer blend of the invention can be performed at room temperature during a time range of about 30 min. A concentration range of the polymer blend is preferably in the range of 0.225 to 5% by weight, more preferred about 0.3 to 0.7% by weight. According to the process of the invention the biocompatible surfactant is an anionic derivative of cholesterol particularly cholesterol 3-sulfate. The surfactant in the oily phase of the dispersion is in the range of 0.01 to 0.2% by weight, preferably about 0.05% by weight. The surfactants are preferably low range hydrophilic/lipophilic balanced compounds (HLB).

The drug which can be used according to the invention is a low molecular lipophilic compound or polypeptide. For example, a low molecular weight drug such as diazepam or antibiotics, anesthetics or antimitotics can be taken into account. The polypeptide could be a peptide or protein including enzymes or antigen molecules such as bovine serum albumin (BSA) or somatotropin or tetanus toxoid, influenza virus and the like. Also drug combinations can be used in the process of invention, for example, diazepam/somatotropin.

The drug loading depends on the nature of the substance and is typically in the range of 0.2 to 20% by weight based on the amount of polymer, preferably about 10% by weight. Depending on the solubility and stability of the drugs to be loaded to the nanoparticles they can be initially solubilized either in water before addition in the organic solution or directly in the organic solution.

Typically, the two phase system in which the nanoparticles are formed is consisting of an oil/aqueous phase. The volume ratio is about 0.7 to 15%, probably 8 to 12%. The dispersion is typically performed using machines e. g. stirrer, rotor-stator equipment or high pressure homogenizer. Preferred is a rotor-stator equipment. The dispersion is carried out at room temperature for 15 sec. to 2 min. The preferred organic solvents are water soluble organic solvents such as DMSO, acetone, tetrahydrofurane, 1,3-dioxolane, N,N-dimethylformamide or mixtures thereof.

The process of the invention can be controlled by changing the polymer concentration in the oil phase, the oil-aqueous phase ratio, the surfactant and its concentration in the oil phase and solvent itself.

Also the composition of the polymer blend (weight ratio of the two polymers) has an effect on the average particle size. According to the invention the process conditions are adjusted that nanoparticles of a size of 0.02 to 1 µm, preferably 50 to 200 nm (average size) are formed. In the process of the invention the separation of nanoparticles in the liquid phase is achieved by filtration or centrifugation. The nanoparticles are separated from the original liquid phase in order to eliminate the organic solvent(s) and the non-encapsulated drug. Preferably, the filtration is carried out at 25° C. with an ultrafiltration membrane, preferably by tangential-ultrafiltration in order to avoid membrane blocking. A suitable membrane is, for example, a cellulosic type membrane of a spiral-type configuration within 0.09 $M^2$ area and a cut off of 100.000. After a first diafiltration cycle nanoparticles are diluted e. g. 2 l of water and purified twice so as to eliminate up to 99.9% of the original solvent. The organic solvent can also be removed from nanoparticles by extraction into the aqueous phase and or ultrafiltration or by evaporation if the organic solvent is sufficiently volatile. Centrifugation is an alternative to the latex filtration when the particles settle down easily without any aggregation.

It may be advantageous to add a polymer such as polyethyleneglycol and/or a polyoxylene-polyoxylene triblock copolymer for making easier redispersion of the nanoparticles after they have undergone a freezedrying. The additive concentration in latex suspension is in a range of 2 to 10% by weight, preferably 3 to 5% by weight.

The invention allows production of biocompatible and biodegradable pseudolatex particles with a homogenous size below 140 nm. The nanoparticles of the invention advantageously show efficient immobilization of proteinaceous drugs by preserving their activity and allowing for their controlled release. The nanoparticles of the invention are stable colloidal carriers against environmental attacks such as pH modifications or freezing or freezedrying processes. All excipients of the formulation are biocompatible for parenteral uses. The polymer blend of the present invention is used for the preparation of colloidal vectors. The polymer blend of the invention has specific properties in terms of solubility, viscosity and in terms of protein interaction. The nanoparticles prepared by the polymeric blend of the invention can advantageously be used for administering proteinaceous drugs. By using the polymeric blend of the invention the activity of the immobilized protein can be kept.

The nanoparticles of the invention can be applied in methods of treating patients with drugs or the drug combinations. Thereby, the drugs or drug combinations are adhered on/or incorporated in nanoparticles. They are administered to patients in need of the drugs associated with the nanoparticles orally, intraperitoneally, topically, intranasally, intravenously in amounts to give an active dose. Examples of treatments are clinical applications such as diabetes and tumor treatment, inflammation and intracellular infection treatment (ophthalmic delivery e.g. pilocarpine, anti tumor drugs and so on), targeting towards inflammation in the body, adjuvant for vaccine, vaccine controlled delivery (e.g. HIV virus or influenza).

BRIEF DESCRIPTION OF THE DRAWINGS

FIG. 5 shows the in vitro release of somatotropin (ST). The I-125 and radio-immuno-assay (RIA) curves correspond to the total and active form of the protein released respectively (cumulative curves).

The invention is further explained by the following examples.

EXAMPLES

Example 1

Nanoparticles Prepared from a Poly(D,L)lactide-co-glycolide Poloxamer Blend and Used to Immobilize Somatotropin 225 mg of a poly (D,L)lactide-co-glycolide copolymer (50 mol %; Mn : 20,000; designated as PLGA) and 225 mg of a polyoxyethylene-polyoxypropylene-polyoxyethylene triblock copolymer (Poloxamer : Pluronic F68) were dissolved in 5 ml of methylene chloride at room temperature for 15 min. The organic solvent was let to evaporate under nitrogen, at room temperature and then to 40° C. This polymer blend could be used immediately or stored at 4° C. for several days under dry conditions.

Cholesterol 3-sulfate (25 mg) was added to the polymer blend followed by 50 ml of DMSO (p.a.). Dissolution took place for 25 min. at room temperature. Somatotropin (25 mg of a lyophilisate powder) was added to the organic solution and dissolved (5 min). This organic solution was dispersed for 2 min. in 700 ml of water with a rotor-stator equipment (Ultra-turrax; IKA Werke, Janke and Kunkel GmbH & Co. KG, Staufen, Germany; S25N-18g drive unit, 24,000 rpm). The suspension obtained was diluted by water until a total volume of 2 l, and then purified by ultrafiltration by using a tangential ultrafiltration equipment (Spiral membrane Amicon, Inc., Beverly, MA, USA, model S1Y100) and a peristaltic pump (model CH2, Amicon, inlet flow rate: 2 l/min; inlet and back-pressure : respectively : 10 and 8 psi). After a first diafiltration cycle, nanoparticles were diluted in water (2 l) and purification was repeated in order to completely eliminate DMSO and the free protein. The latex suspension was concentrated: final volume of e. g. 100 ml. The suspension was used either immediately or added $NaN_3$ (0.001%) and stored at 4° C. It can also be freezed or freezed-dried after the addition of the poloxamer: Pluronic F68(4 wt-%). The total amount of polymer in the final latex suspension was ca. 40% of the original amount.

The somatotropin immobilization efficiency was 90%. The total amount of protein immobilized was measured by using an iodinated (I-125) form of somatotropin and measuring the I-125 associated with the latex. The immobilization efficiency of the active protein was ca. 30 to 40%. Activity of the protein was assessed by radio-immuno-assay (RIA) either directly on the latex suspension, or after lyophilization of the latex dissolution in DMSO, or from the total amount released protein (see next section).

Figure 1:
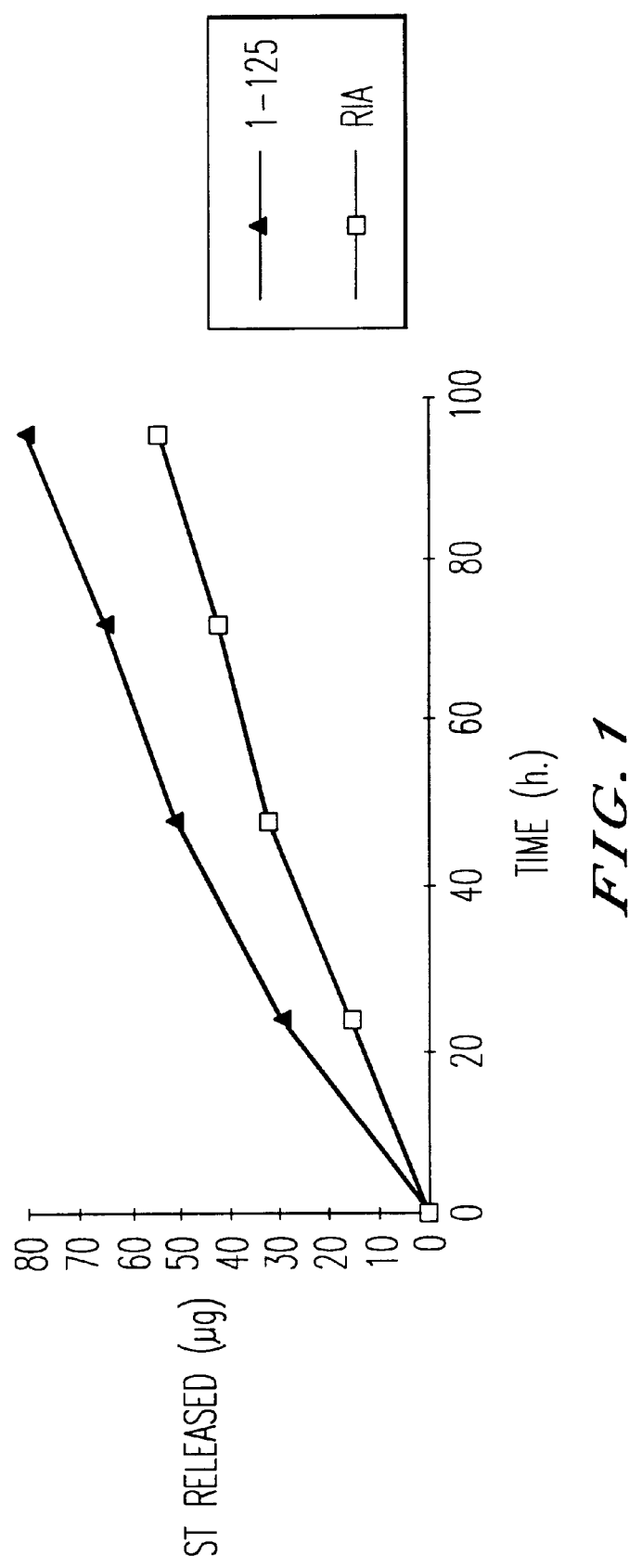
FIG. 1 shows the in vitro release of somatotropin (ST). The I-125 and radio-immuno-assay (RIA) curves correspond to the total and active form of the protein released respectively (cumulative curves).
Figure 2:
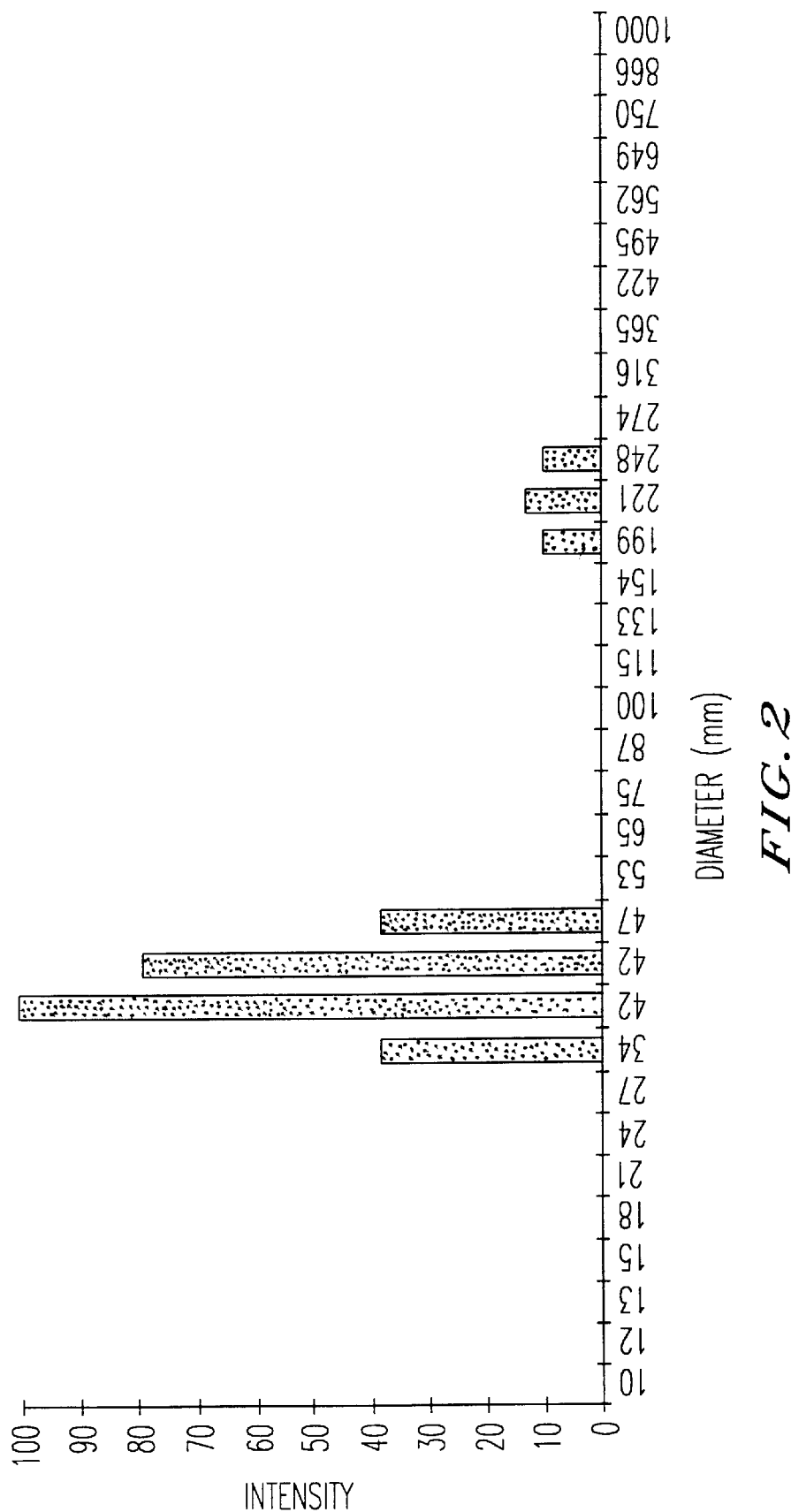
FIG. 2 shows the size distribution of PLGA-F68 nanoparticles measured by PCS.

The rate of the protein released was measured at 12° C. by dialysis (membrane of a 100,000 Da cut-off: Spectra/Por Cellulose Ester membrane, Spectrum, Houston, Tex. USA). Nanoparticles were stored in the dialysis bag, and release of the protein was measured against a sodium phosphate buffer (10 mM, pH 7.4) containing serum albumin bovine (1 wt-%) and $NaN_3$ (0.02%). This solution was replaced every day (4 ml of latex suspension compared to 6 ml of external buffer). The protein concentration in the external buffer was measured by RIA (active form) and by the amount of I-125 associated with the released iodinated protein (total amount). Kinetics of in vitro release are shown in FIG. 1. The size of the particles was measured by dynamic light scattering (or PCS) (FIG. 2).

Example 2

Figure 3:
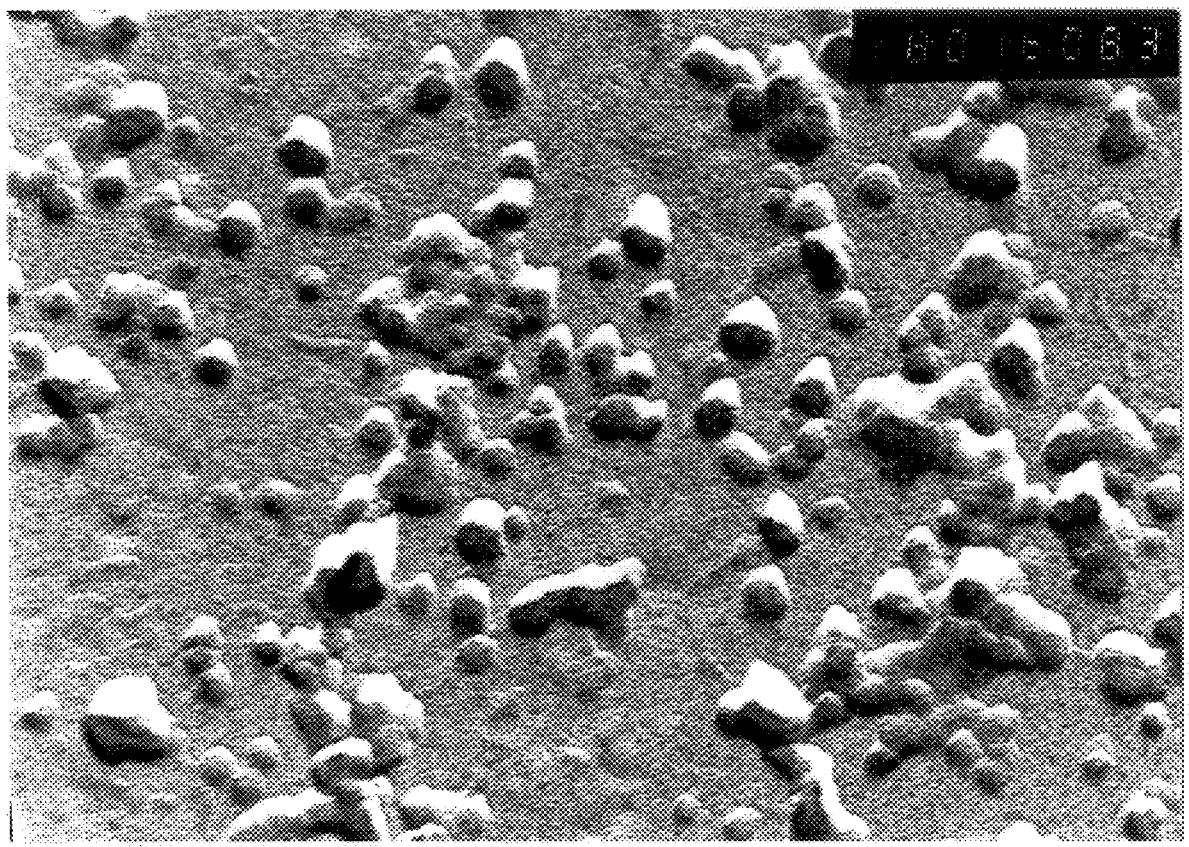
FIG. 3 shows a micrograph (TEM) of nanoparticles.
Figure 4:
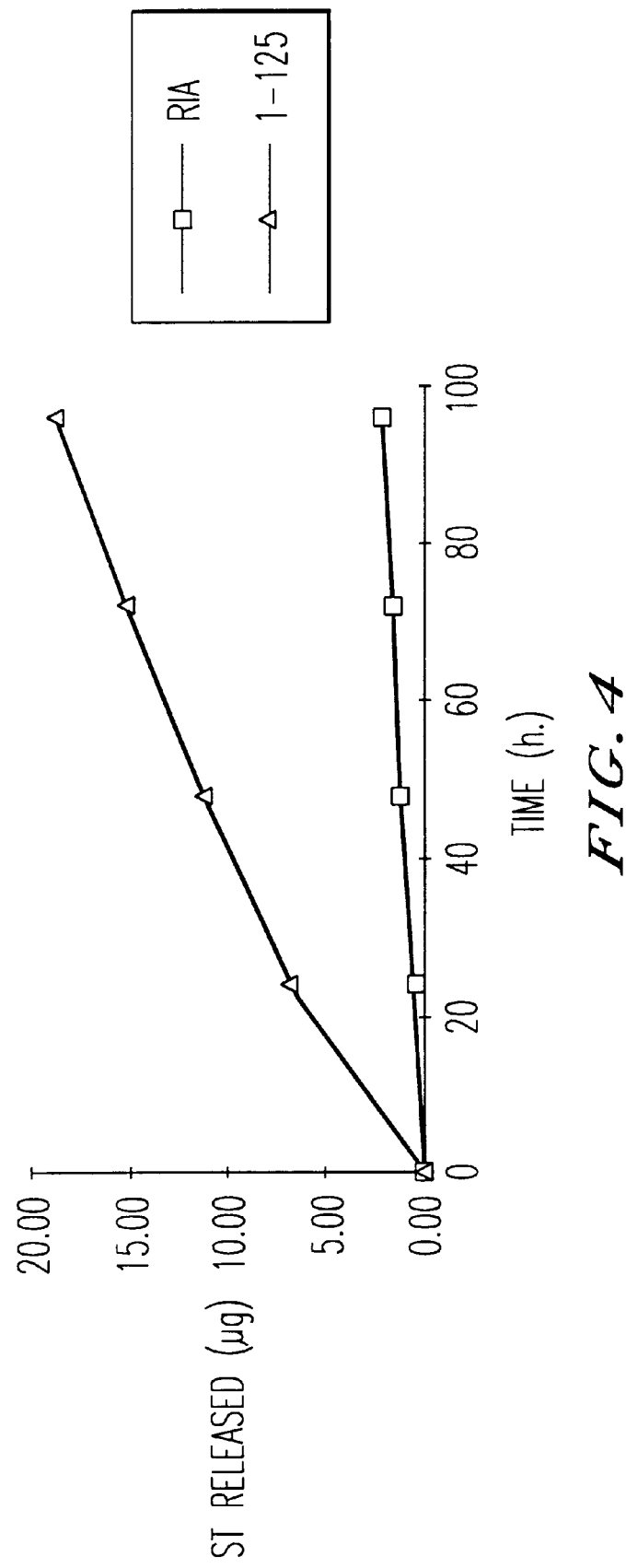
FIG. 4 shows in vitro release of somatotropin (ST). The I-125 and RIA curves correspond to the total and active form of the protein released respectively (cumulative curves).

Nanoparticles Prepared from Poly(D,L)Lactide and Used to Immobilize a Somatotropin In this case poly (d,l)lactide-co-glycolide was used alone, thus without any biocompatible interacting agents such as in example 1. The mean size of the latex, as analyzed by PCS and transmission electron microscopy (FIG. 3) was smaller: 70 nm compared to 100 to 140 nm for the poly(d,l)lactide-coglycolide/Pluronic F68 blend. This size has been verified by transmission electron microscopy (FIG. 3). FIG. 4 shows that the protein was released essentially as an inactive compound.

Example 3

225 mg of PLGA, 22,5 mg of poly [HEMA-g-(D,L)-polylactide] graft copolymer, and 25 mg of cholesterol sulfate were dissolved in 50 ml of DMSO (p.a.). Dissolution and oil in water dispersion were performed as described in example 1. As can be seen from FIG. 5 the protein is also released essentially as an active compound similarly to Example 1.

What is claimed is:

1. Nanoparticles for proteinaceous drugs or peptides with a homogenous particle size between 50 and 200 nm, containing:

(a) a biocompatible polymer selected from the group consisting of polyεcaprolactone, polylactide, polyglycolide, and copolymers thereof, (b) a biocompatible interacting agent selected from the group consisting of polyethyleneglycol, and polyoxyethylene-polyoxypropylene-polyoxyethylene triblock copolymer having the general formula

$HO(C_2H_4O)_a(C_3H_6O)_b(C_2H_4O)_aH$ wherein a and b are selected to give a number-average molecular weight of the total interacting agent in the range of some hundreds to 20,000 Da, or an amphilic graft copolymer containing a hydrophilic backbone grafted with hydrophobic aliphatic polyester subchains, (c) a cholesterol or anionic cholesterol derivative as a biocompatible surfactant, and (d) a low molecular lipophilic compound and/or a polypeptide as a drug, wherein (a), (b), (c) and (d) form a homogeneously mixed blend.

2. The nanoparticles of claim 1, wherein the biocompatible polymer is a polylactide.

3. The nanoparticles according to claim 1, wherein the drug is an oligo- or polypeptide or a mixture of an oligo- or polypeptide with a low or high molecular weight biologically active substance.

4. The nanoparticles of claim 1, wherein the peptide drug is selected from the group consisting of enzymes, antigen molecules, bovine serum albumin, somatotropin, tetanus toxoid, and influenza virus.

5. A process for preparing the nanoparticles of claim 1, comprising mixing the biocompatible polymer and the biocompatible interacting agent in an organic solvent, mixing the solution and evaporating the solvent to form a homogenously mixed blend, or melting one of the components and adding the other component so that an essentially homogenous mixture is built up, or melting both components together and forming an essentially homogenous mixture, dissolving the polymer blend in a water soluble organic solvent selected from the group consisting of dimethyl sulfoxide, acetone, tetrahydrofurane, 1,3-dioxolane, N,N-dimethylformamide, and mixtures thereof adding a biocompatible surfactant, adding a drug or a drug combination, wherein these steps are conducted in such a manner that the mixture of polymer blend, surfactant and drug or drug combination form an essentially homogenous mixture, contacting the mixture with an aqueous phase to form a dispersion, and separating the formed nanoparticles from the liquid phase, and optionally freeze-drying the nanoparticles after separation.

6. The process of claim 5, wherein the separation of nanoparticles and the liquid phase is achieved by filtration, centrifugation or wherein the organic solvent is removed from the nanoparticles by extracting into the aqueous phase and/or removing the liquid phase by ultra filtration or removing the liquid phase by evaporation if the organic solvent is sufficiently volatile.

7. The process of claim 5, wherein a polymer is added for making easier re-dispersion of the nanoparticles after freeze drying of the nanoparticles.

8. The process of claim 5, wherein the polymer is polyethylene glycol and/or polyoxyethylene-polyoxypropylene-polyoxyethylene triblock copolymer.

9. The process of claim 5, wherein the reaction mixture after partitioning is frozen.

10. The process of claim 5, wherein the peptide drug is selected from the group consisting of enzymes, antigen molecules, bovine serum albumin, somatotropin, tetanus toxoid, and influenza virus.

11. A method of treating patients with drugs or drug combinations adhered on or incorporated in nanoparticles of claim 1 by administering said nanoparticles to patients in need of the drugs associated with nanoparticles orally, intraperitoneally, topically, intranasally, intravenously in amounts to give an active dose.

* * * * *